(12) United States Patent
Huang (10) Patent No.: US 7,129,845 B2
(45) Date of Patent: Oct. 31, 2006

(54) ELECTROTHERAPEUTIC APPARATUS FOR PROGRAMMING AND MEMORIZING MODULATED MEDIUM FREQUENCY CARRIER WAVES

(76) Inventor: Chih Jung Huang, No. 53, Dan-Shan 4th Road, Shiau-Gang Dist., Kaohsiung City (TW)

( * ) Notice: Subject to any disclaimer, the term of this patent is extended or adjusted under 35 U.S.C. 154(b) by 170 days.

(21) Appl. No.: 10/983,787

(22) Filed: Nov. 9, 2004

(65) Prior Publication Data

US 2005/0107830 A1    May 19, 2005

(30) Foreign Application Priority Data

Nov. 18, 2003    (TW)    ............................... 92132228 A (51) Int. Cl.
   *G08B 23/00* (2006.01)
   *A61H 1/00* (2006.01)
(52) U.S. Cl. .................. 340/573.1; 601/46; 601/84
(58) Field of Classification Search ............ 340/573.1; 601/46, 47, 48, 53, 54, 84, 89
   See application file for complete search history.

(56) References Cited

U.S. PATENT DOCUMENTS

| 4,232,661 A | * | 11/1980 | Christensen | ................. | 601/48 |
| 4,779,615 A | * | 10/1988 | Frazier | ......................... | 601/47 |
| 5,113,852 A | * | 5/1992 | Murtonen | ..................... | 601/47 |
| 5,437,608 A | * | 8/1995 | Cutler | .......................... | 601/49 |
| 5,951,500 A | * | 9/1999 | Cutler | .......................... | 601/47 |
| 6,001,073 A | * | 12/1999 | Schmidt et al. | ............... | 601/72 |
| 6,027,463 A | * | 2/2000 | Moriyasu | ..................... | 601/46 |
| 6,547,749 B1 | * | 4/2003 | Hansen | ........................ | 601/48 |
| 6,770,042 B1 | * | 8/2004 | Lee | ............................... | 601/47 |
| 7,056,297 B1 | * | 6/2006 | Dohno et al. | .................. | 601/48 |

* cited by examiner

*Primary Examiner*—John A. Tweel, Jr.
(74) *Attorney, Agent, or Firm*—Rosenberg, Klein & Lee (57) ABSTRACT

An electrotherapeutic apparatus for programming and memorizing modulated medium frequency carrier waves is disclosed. The electrotherapeutic apparatus comprises: a central processing unit; a program-memorizing unit, a data-memorizing unit, a data input unit, an alarm/output unit, an editing and display unit, a signal transformation unit, a signal output driving unit, a signal output display unit, a signal output actuation unit, and an overvoltage protection unit. The electrotherapeutic apparatus is able to memorize groups of modulated waves for use in deep/shallow positions, physical causes, and physiotherapeutic procedures of various diseases. The formulas for deep/shallow positions, physical causes, and physiotherapeutic requirements of various diseases can be formed respectively. In the formation of physiotherapeutic procedures and formulas, data can be modified and stored in the data-memorizing unit according to various ill positions so as to provide with suitable and accurate therapeutic procedures.

15 Claims, 11 Drawing Sheets

ELECTROTHERAPEUTIC APPARATUS FOR PROGRAMMING AND MEMORIZING MODULATED MEDIUM FREQUENCY CARRIER WAVES

FIELD OF THE INVENTION

The present invention relates to an electrotherapeutic apparatus for programming and memorizing modulated medium frequency carrier waves, and more particularly to an electrotherapeutic apparatus that performs modulation steps in accordance with deep/shallow positions, physical causes, and physiotherapeutic requirements of various diseases so as to edit or modify data (formulas), which are thereafter stored in the data-memorizing unit. Furthermore, the electricity is transformed for use in the therapeutic procedure so as to provide with optimum electrotherapeutic efficacy.

BACKGROUND OF THE INVENTION

In general, commercial electrotherapeutic apparatuses nowadays generally perform the physiotherapeutic procedures by outputting a pulse signal in a single mode or a fixed mode. However, if these conventional physiotherapeutic procedures are adopted, it is impossible for the doctor to exactly recognize ill positions and therapeutic efficacy since different patient require different therapeutic treatments for different deep/shallow positions, physical causes, and physiotherapeutic requirements of diseases. As a result, these conventional physiotherapeutic procedures, which output a pulse signal in a single mode or a fixed mode, do not satisfy practical requirements of users.

Moreover, the current electrotherapeutic apparatuses perform the physiotherapeutic procedures in such an asynchronous signal manner that two unequal signal outputs and asynchronous signal speeds are applied simultaneously to the ill positions of the patient. Since the general public are short of cognition and common sense related to electricity and the physiotherapeutic procedures are performed in such an asynchronous signal manner that two unequal signal outputs and asynchronous signal speeds are applied, the patient always suffers from fear caused by bodily and mental burdens.

Furthermore, a pulse signal actuation device of the current electrotherapeutic apparatuses is a contact switch. There are formed more or less surges at the moment of turning on or off the contact switch, wherein the surges always make the patient unconformable. Consequentially, the current electrotherapeutic apparatuses do not satisfy practical requirements of users.

SUMMARY OF THE INVENTION

Accordingly, one aspect of the present invention is to provide formulas for use in deep/shallow positions, physical causes, and physiotherapeutic requirements of various diseases by means of modulated medium frequency carry waves so as to supply with optimum electrotherapeutic efficacy.

Another aspect of the present invention is to modify and store data in the data-memorizing unit so as to provide with suitable and accurate therapeutic procedures in accordance with various ill positions.

Still another aspect of the present invention is to directly apply the medium frequency waves (medium frequency square waves) to the human body and permeate the modulated low frequency waves, extremely low frequency waves (modulated waves) into the human body in accordance with magnitude variations of the medium frequency waves. As a result, greater electrotherapeutic efficacy can be provided for the deeper portion of the human body during the physiotherapeutic procedure.

Still another aspect of the present invention is to enable the patient and the doctor to exactly interact with one another so as to bring the electrotherapeutic efficacy into full play. As a result, therapeutic expenses can be saved and the duration of the therapeutic procedure can be significantly shortened.

According to one aspect of the present invention, an electrotherapeutic apparatus for programming and memorizing modulated medium frequency carrier waves is disclosed. The electrotherapeutic apparatus comprises: a central processing unit that is adopted as an operation of the electrotherapeutic apparatus; a program-memorizing unit, connected to the central processing unit for storing program (software), wherein the program-memorizing unit is mounted inside or outside the central processing unit to form an internal program-memorizing unit and an external program-memorizing unit respectively; a data-memorizing unit, electrically connected with the central processing unit for storing data of modulated wave groups and various therapeutic procedures; a data input unit, electrically connected with the central processing unit for choosing or editing the data of the modulated wave groups stored in the data-memorizing unit; an alarm/output unit, electrically connected with the central processing unit for warning and outputting a status of the electrotherapeutic apparatus; an editing and display unit, electrically connected with the central processing unit for displaying the data of the modulated wave groups stored in the data-memorizing unit; a signal transformation unit, electrically connected with the central processing unit for performing the digital/analog conversion step on the data of the modulated wave groups so as to form the modulated wave groups; a signal output driving unit, electrically connected with the signal transformation unit, for driving the signal transformation unit by outputting synchronous signals; a signal output display unit, electrically connected with the signal transformation unit, for displaying the signal output statuses of the electrotherapeutic apparatus; a signal output actuation unit, electrically connected with the central processing unit and the signal output driving unit respectively, wherein the central processing unit drives the signal output actuation unit to utilize two independent signal output ports to permit or forbid outputting the signals; and an overvoltage protection unit, which is electrically connected with the central processing unit and the signal output actuation unit respectively, wherein when the supplied power is unstable or an interference source generates a surge, the signal output actuation unit will be terminated to stop outputting the signals to avoid the overvoltage phenomenon. As a result, it is possible to apply the data-memorizing unit to memorize the modulated waves for forming formulas of various therapeutic treatments for use in deep/shallow positions, physical causes, and physiotherapeutic requirements of various diseases. Besides, it is possible to provide various pathological formulas respectively for various therapeutic treatments for deep/shallow positions, physical causes, and physiotherapeutic requirements of various diseases. In the formation of physiotherapeutic procedures and formulas, data can be modified and stored in the data-memorizing unit so as to provide with suitable and accurate therapeutic procedures.

Furthermore, the electricity is transformed for use in the therapeutic procedure so as to provide with optimum electrotherapeutic efficacy.

DETAILED DESCRIPTION OF THE PREFERRED EMBODIMENT

Figure 1:
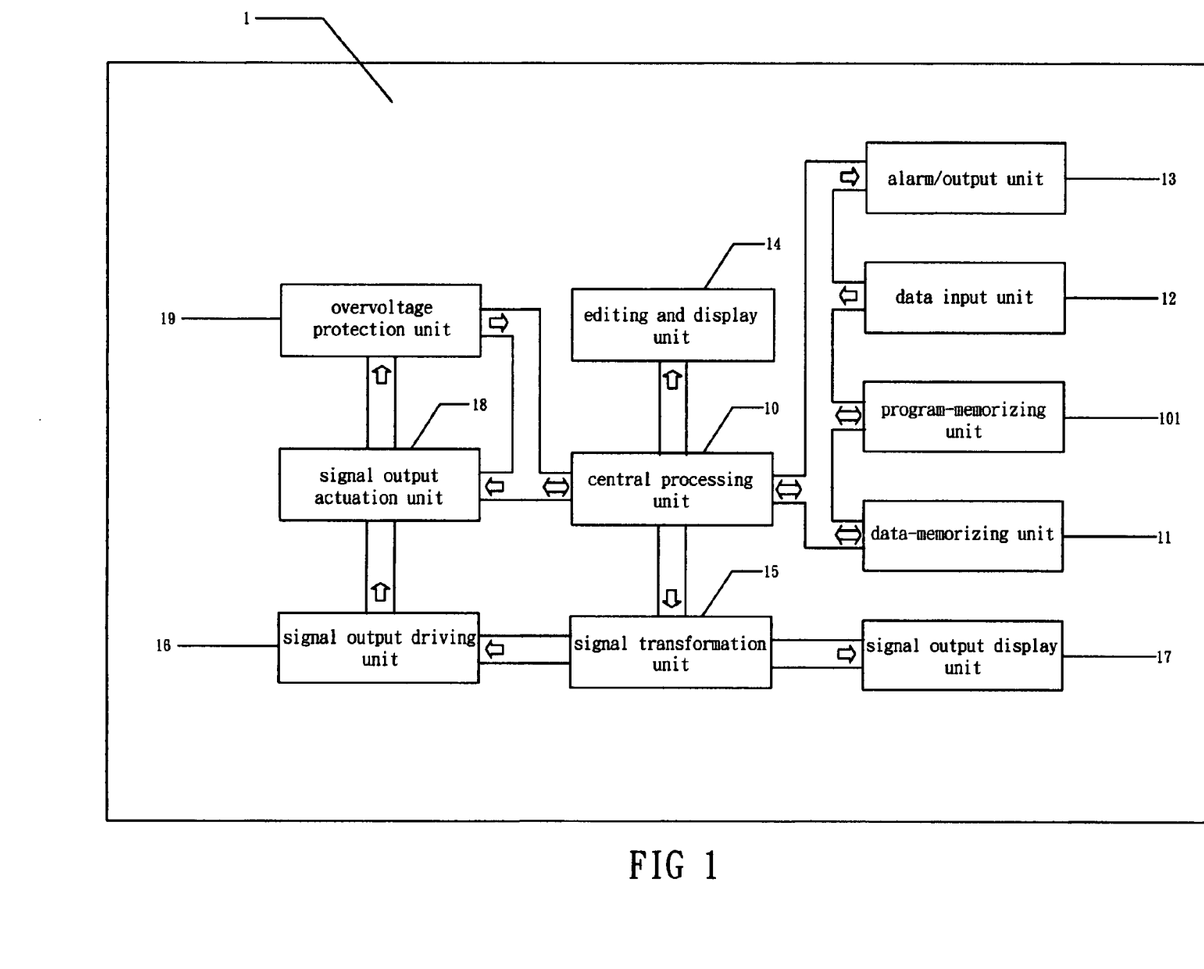
FIG. 1 is a schematic view of a skeleton of the present invention.
Figure 2:
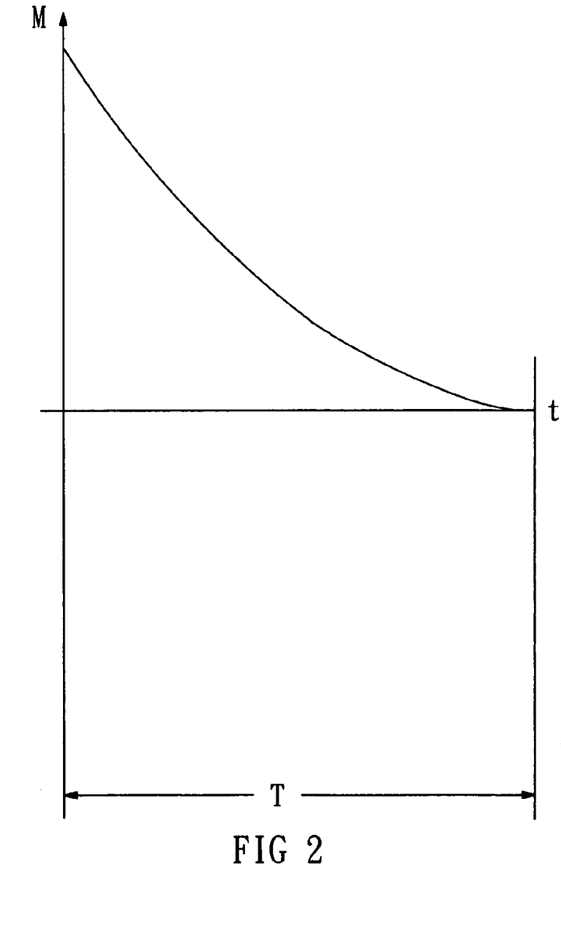
FIG. 2 is a schematic view of a polynomial function diagram of a modulating wave group of the present invention.
Figure 3:
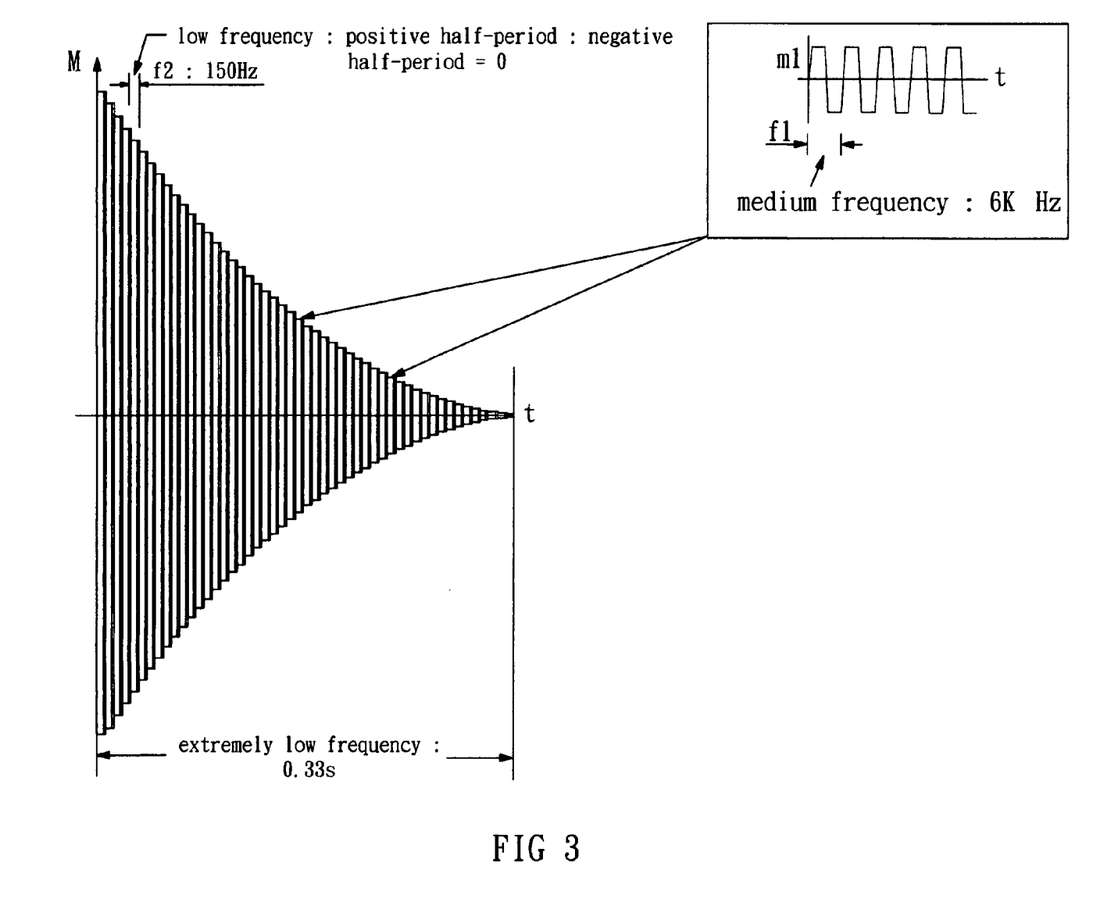
FIG. 3 is a schematic view showing an intermittently modulated medium frequency carrier wave of the present invention.
Figure 4:
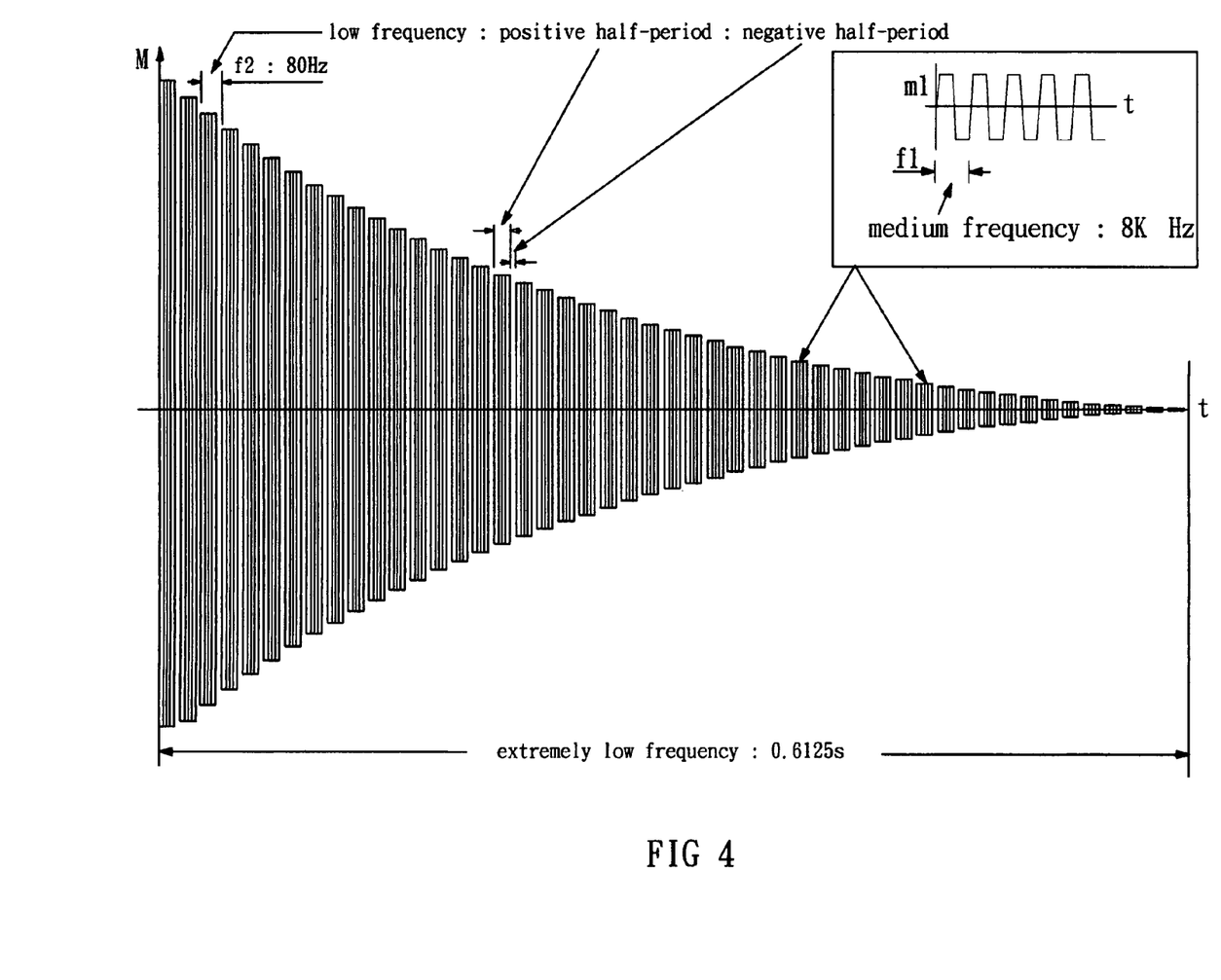
FIG. 4 is a schematic view showing a discontinuously modulated medium frequency carrier wave of the present invention.
Figure 5:
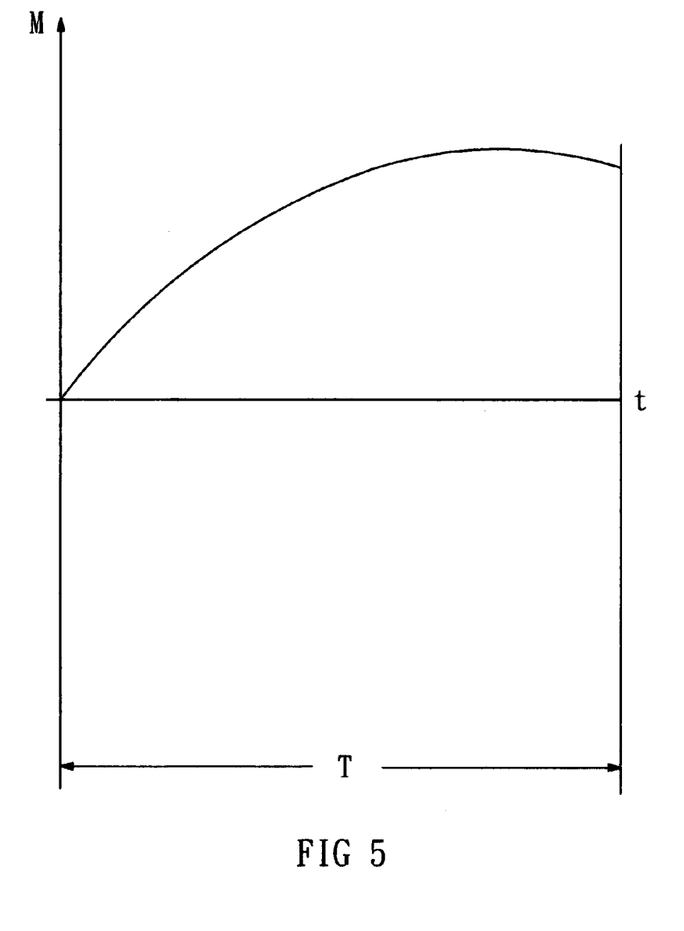
FIG. 5 is a schematic view of a polynomial function diagram of a modulating wave group of the present invention.
Figure 6:
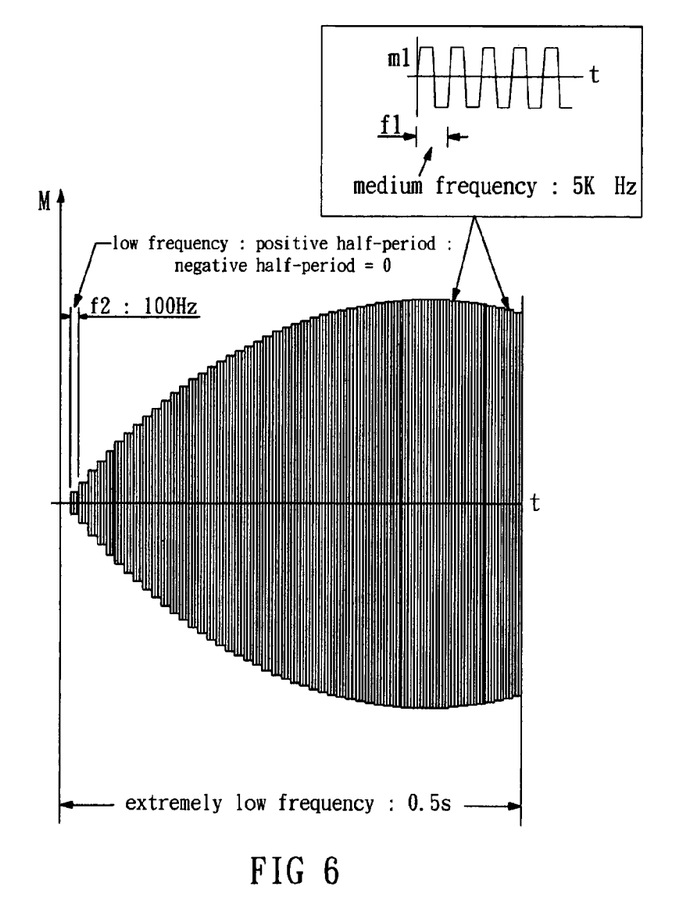
FIG. 6 is a schematic view showing an intermittently modulated medium frequency carrier wave of the present invention.
Figure 7:
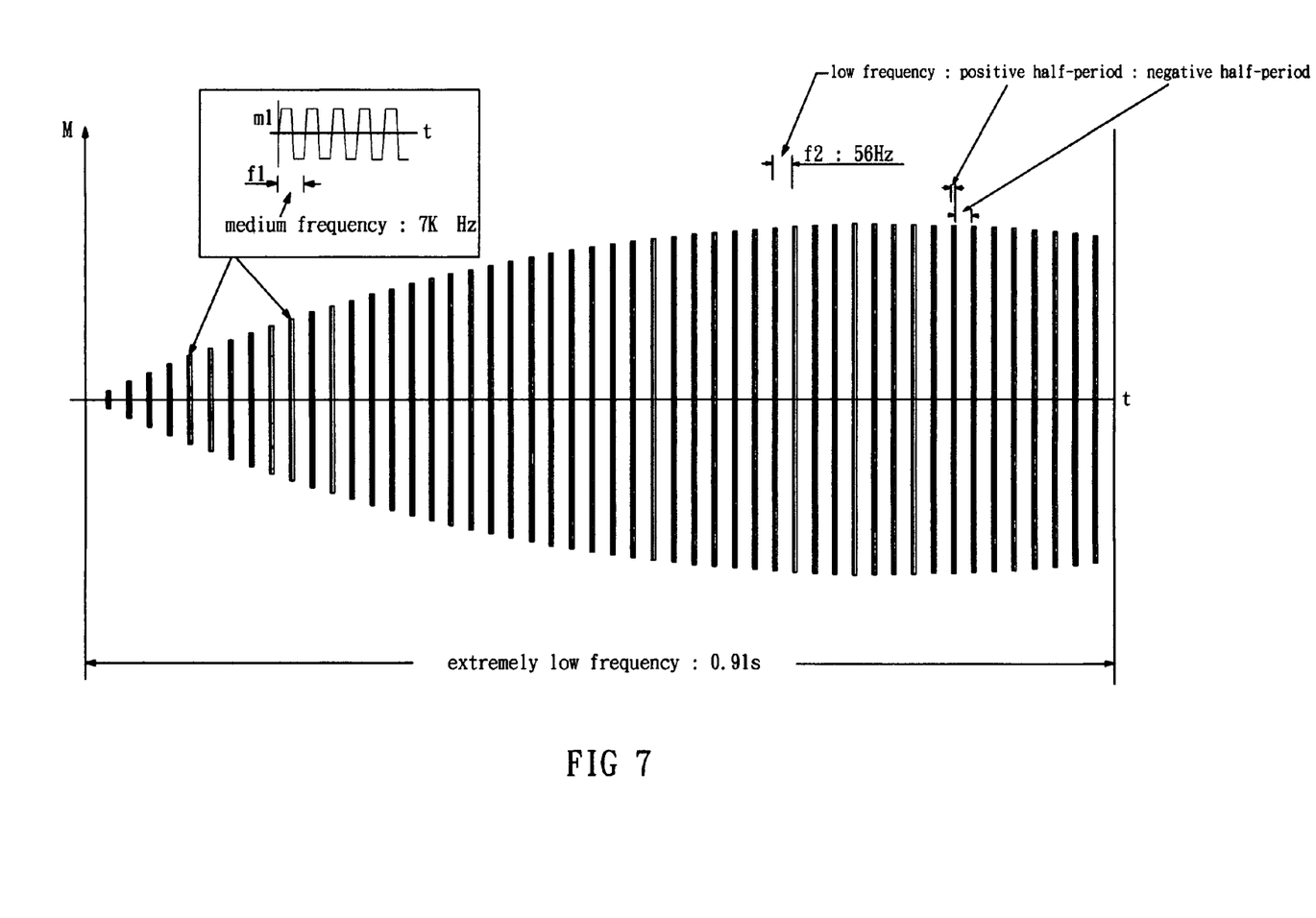
FIG. 7 is a schematic view showing a discontinuously modulated medium frequency carrier wave of the present invention.
Figure 8:
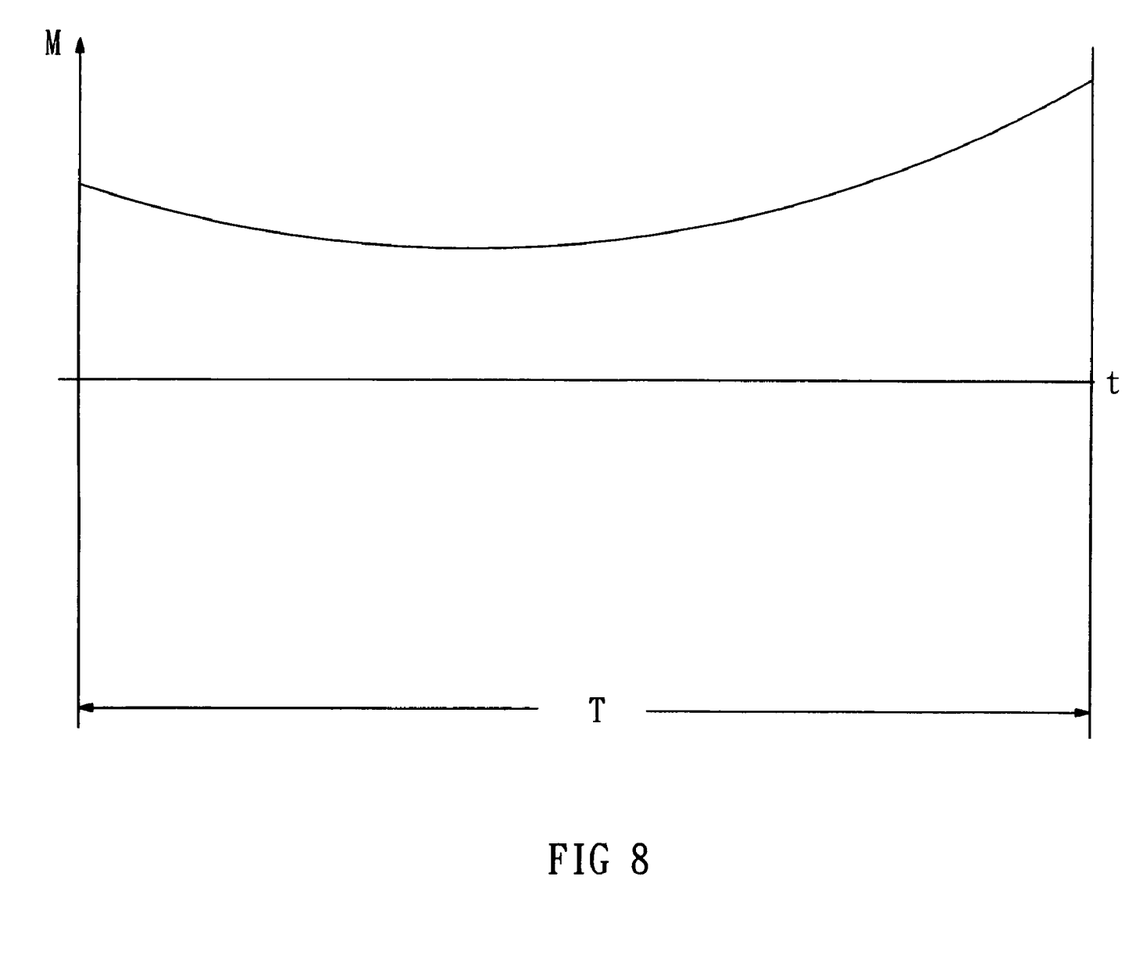
FIG. 8 is a schematic view of a polynomial function diagram of a modulating wave group of the present invention.
Figure 9:
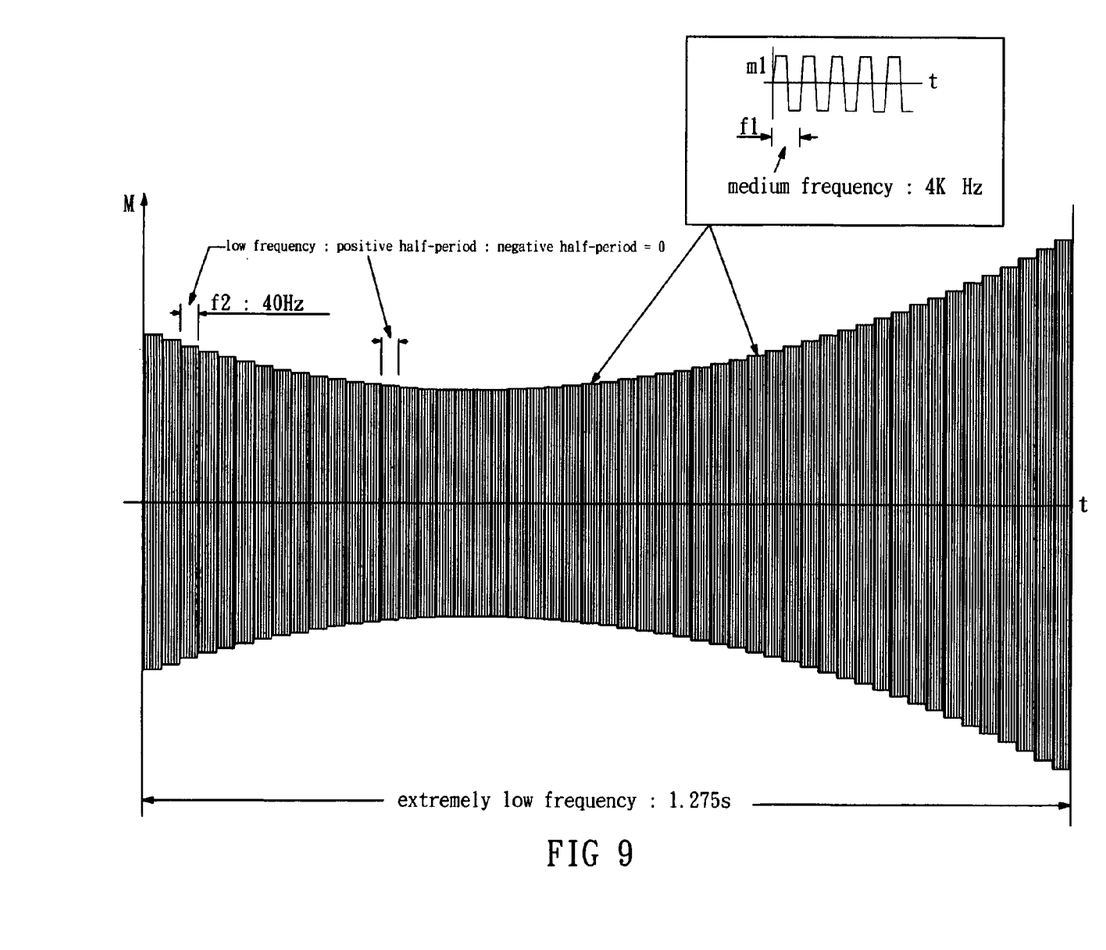
FIG. 9 is a schematic view showing an intermittently modulated medium frequency carrier wave of the present invention.
Figure 10:
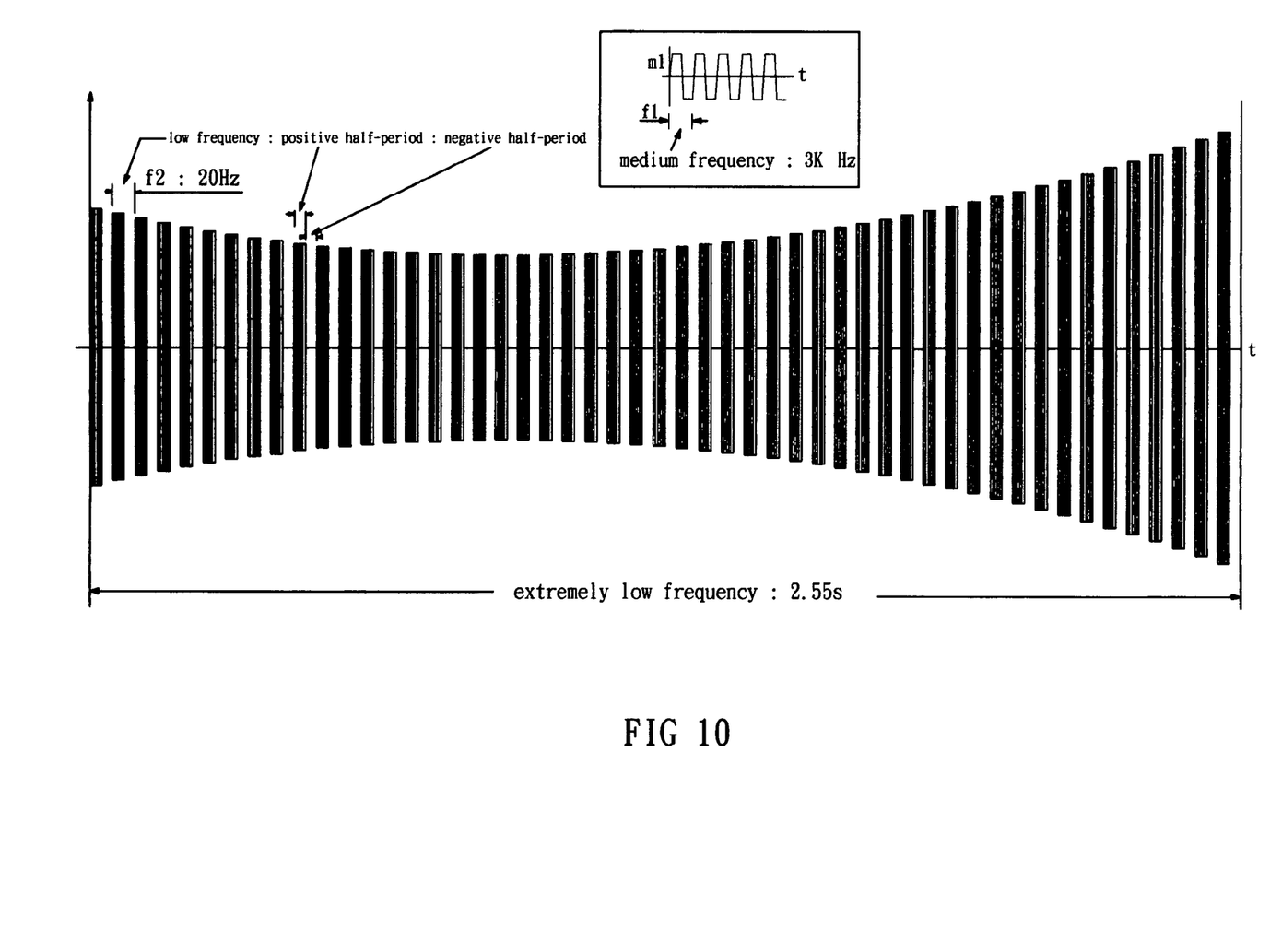
FIG. 10 is a schematic view showing a discontinuously modulated medium frequency carrier wave of the present invention.

FIG. 1 is a schematic view of a skeleton of the present invention. FIG. 2 is a schematic view of a polynomial function diagram of a modulating wave group of the present invention. FIG. 3 is a schematic view showing an intermittently modulated medium frequency carrier wave of the present invention. FIG. 4 is a schematic view showing a discontinuously modulated medium frequency carrier wave of the present invention. FIG. 5 is a schematic view of a polynomial function diagram of a modulating wave group of the present invention. FIG. 6 is a schematic view showing an intermittently modulated medium frequency carrier wave of the present invention. FIG. 7 is a schematic view showing a discontinuously modulated medium frequency carrier wave of the present invention. FIG. 8 is a schematic view of a polynomial function diagram of a modulating wave group of the present invention. FIG. 9 is a schematic view showing an intermittently modulated medium frequency carrier wave of the present invention. FIG. 10 is a schematic view showing a discontinuously modulated medium frequency carrier wave of the present invention.

Referring to FIG. 1 through FIG. 10, the present invention relates to an electrotherapeutic apparatus 1 for programming and memorizing modulated medium frequency carrier waves. This electrotherapeutic apparatus 1 produces modulated waves by modulating medium frequency carrier waves. The modulated waves are applied to physiotherapeutic procedures, acupuncture points, health care, breast enhancing, muscle training, and massage. The electrotherapeutic apparatus comprises a central processing unit 10, a program-memorizing unit 101, a data-memorizing unit 11, a data input unit 12, an alarm/output unit 13, an editing and display unit 14, a signal transformation unit 15, a signal output driving unit 16, a signal output display unit 17, a signal output actuation unit 18, and an overvoltage protection unit 19. The data-memorizing unit 11 is applied to memorize groups of modulated waves for use in deep/shallow positions, physical causes, and physiotherapeutic procedures of various diseases. The formulas of various therapeutic treatments for deep/shallow positions, physical causes, and physiotherapeutic requirements of various diseases can be formed respectively. Moreover, in the formation of pathological procedures and formulas, data can be modified and stored in the data-memorizing unit 11 according to various ill positions so as to provide with suitable and accurate therapeutic procedures. In addition, the medium frequency waves (medium frequency square waves) can be directly applied to the human body. The modulated low frequency waves and extremely low frequency waves (modulated waves) are able to permeate into the human body in accordance with magnitude variations of the medium frequency waves. As a result, a greater electrotherapeutic efficacy can be provided for the deeper portion of the human body during the physiotherapeutic procedure.

The central processing unit 10 is adopted as an operation center of all units of the electrotherapeutic apparatus 1. The central processing unit 10 also cooperates with a program-memorizing unit 101, which is applied to store program (software). The program-memorizing unit 101 is mounted inside the central processing unit 10 to form an internal program-memorizing unit 101. Alternatively, the program-memorizing unit 101 is mounted outside the central processing unit 10 and electrically connected to thereof to form an external program-memorizing unit 101.

The data-memorizing unit 11 is electrically connected with the central processing unit 10 described above for storing data of modulated wave groups of modulated low frequency waves and extremely low frequency waves (modulated waves) and various therapeutic procedures. As a result, the present invention is able to adopt the digital programmable and memorizeable method to form various pathological formulas respectively. After they are formed, a corresponding physiotherapeutic procedure can be further formed according to an individual formula. Moreover, in the formation of physiotherapeutic procedures and formulas, data can be modified and stored in the data-memorizing unit 11 according to various ill positions so as to provide with suitable and accurate therapeutic procedures. In other words, the formulas are formed first, and the therapeutic procedures are thereafter formed in accordance with the formed formulas. In theory, a medium frequency square wave ranged from 2K Hz to 10K Hz is adopted as a carrier wave, and the carrier wave is then applied to the modulation process to generate a modulated wave at a low frequency (from 2 Hz to 150 Hz) and/or an extremely low frequency (from 0.2 Hz to 2 Hz), or a much lower frequency.

The data input unit 12 is electrically connected with the above central processing unit 10 for choosing or editing the data of the modulated wave groups stored in the data-memorizing unit 11. The data input unit 12 is a push button.

The alarm/output unit 13 is electrically connected with the above central processing unit 10 for warning and outputting the status of the electrotherapeutic apparatus by use of various sounds to indicate various conditions, wherein these sounds are, for example, sounds generated during the actuation of the data input unit 12 and sounds that indicate all conditions during the therapeutic procedure. The alarm/output unit 13 is a speaker.

The editing and display unit 14 is electrically connected with the above central processing unit 10 for displaying the data of the modulated wave groups stored in the data-memorizing unit 11. The editing and display unit 14 is a liquid crystal display monitor.

The signal transformation unit 15 is electrically connected with the above central processing unit 10 for performing the digital/analog conversion step on the data of the modulated wave groups so as to form the modulated wave groups.

The signal output driving unit 16 is electrically connected with the above signal transformation unit 15 to drive the signal transformation unit 15 to perform action.

The signal output display unit 17 is electrically connected with the above signal transformation unit 15 for displaying the signal output statuses of the electrotherapeutic apparatus 1. The signal output display unit 17 is a light emitting diode.

The signal output actuation unit 18 is electrically connected with the central processing unit 10 and the signal output driving unit 16 respectively, wherein the central processing unit 10 drives the signal output actuation unit 18 to utilize two independent signal output ports through the signal output driving unit 16 to output synchronous signals and perform the physiotherapeutic procedures by use of equalized signal outputs and synchronized signal speeds. As a result, it reduces bodily and mental burdens on a patient who undergoes the physiotherapeutic procedures and also prevents this person from fear. This signal output actuation unit 18 comprises two independent non-contact switches, the main purpose of which is to permit or forbid outputting the signals. It may be said that the unit 18 is a protection unit that protects the treated patient against the uncomfortableness caused by the unstable electric power and the overvoltage phenomenon, which is generated by an interference source that forms a surge.

The overvoltage protection unit 19 is electrically connected with the central processing unit 10 and the signal output actuation unit 18 respectively. As long as the supplied power is unstable or the interference source generates the surge, the signal output actuation unit 18 will be terminated. As a result, the signal outputs are terminated to avoid the overvoltage phenomenon. The overvoltage protection unit 19 acts as an overvoltage protection device of two independent signal outputs of the above signal output actuation unit 18 so as to avoid the overvoltage phenomenon, which is caused by the unstable electric power or the surge generated by the interference source. If overvoltage occurs, the signal output actuation unit 18 will be terminated immediately so as to stop outputting the signals. As a result, this patient is prevented from the bodily and mental burdens. Consequentially, a new programmable and memorizeable electrotherapeutic apparatus with modulated medium frequency carrier waves is constituted.

For the formation procedure of each modulated wave group of the present invention, a mathematical polynomial equation is applied to transform its function value into a function diagram, wherein this mathematical polynomial equation satisfies the essential condition that it is a time-domain progressive wave equation. Next, a medium frequency carrier wave is modulated by this function diagram (as shown in FIG. 2, FIG. 5, and FIG. 8) to form a wave at a low frequency, an extremely low frequency (as shown in FIG. 3 and FIG. 4, which are corresponding to FIG. 2, FIG. 6 and FIG. 7, which are corresponding to FIG. 5, and FIG. 9 and FIG. 10, which are corresponding to FIG. 8), and/or a much lower frequency.

The formation procedures of the modulated wave groups of the present invention are illustrated through examples shown in FIGS. 3, 4, 6, 7, 9, and 10 in which mathematical polynomial equations are applied to form function diagrams (as shown in FIGS. 2, 5, and 8), wherein the use of various mathematical polynomial equations or the changing of parameter values of these equations forms various function diagrams for the purpose of forming diagrams with infinite changes. Thereafter, these function diagrams (as shown in FIGS. 2, 5, and 8) modulate medium frequency carrier waves to form symmetric waves at low frequencies (the parameters of positive half-period and negative half-period are given). With variation in magnitude (M) of the function diagrams (as shown in FIGS. 2, 5, and 8), waves at extremely low frequencies are thus formed. As long as a modulated wave, which is selected from the modulated wave groups shown in FIGS. 3, 4, 6, 7, 9, and 10, is applied to the human body, it brings about a corresponding electro-biological affect.

Figure 11:
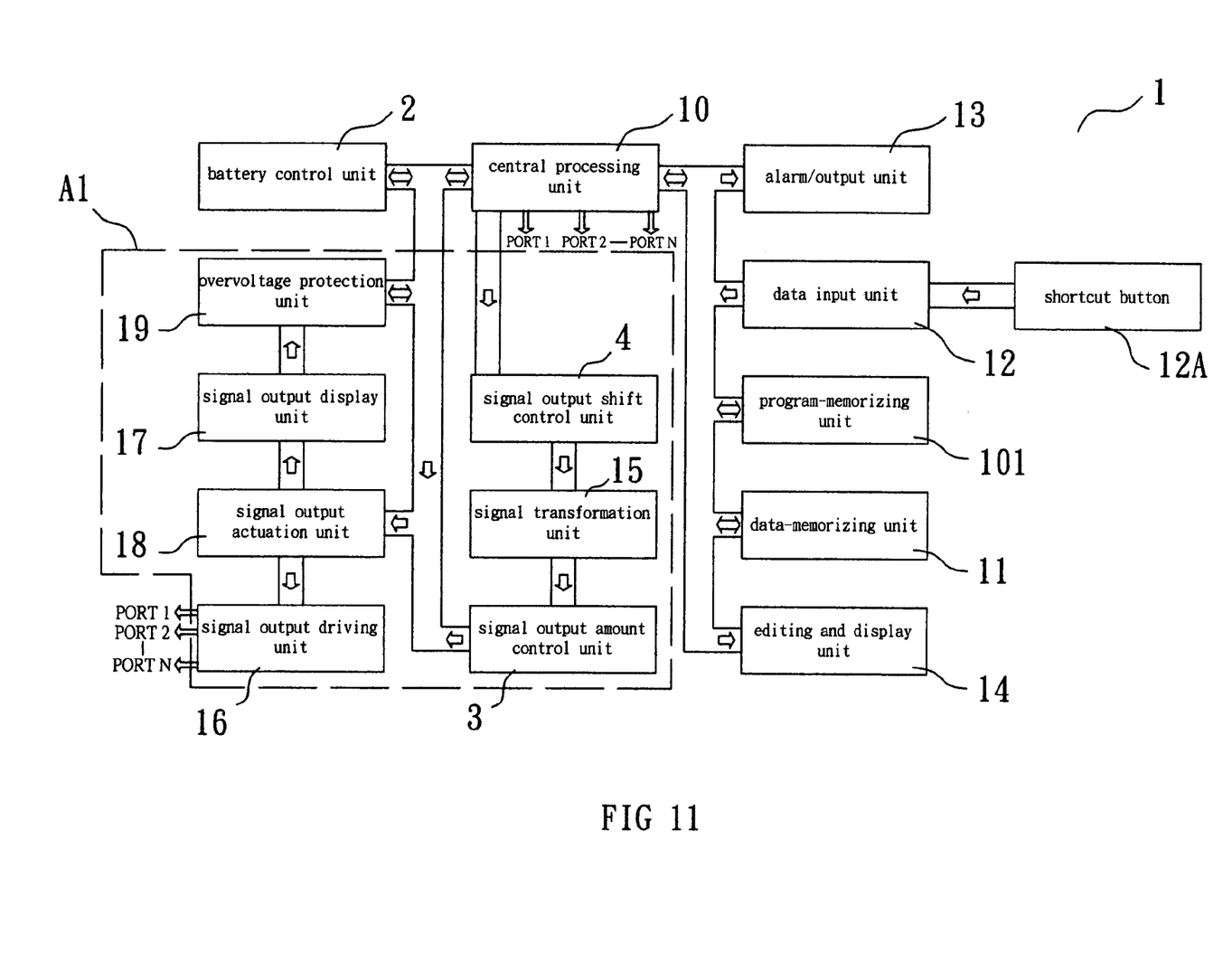
FIG. 11 is a schematic view of a skeleton of another preferred embodiment of the present invention.

In addition, a practicable embodiment of the present invention, as shown in FIG. 11, is derived from the scheme of FIG. 1.

Referring to FIG. 11, the data input unit of the present invention comprises a shortcut button 12A for simplifying the input operation.

The present invention also comprises a battery control unit 2 so as to supply backup power when the power supplied by an electric power service corporation is unstable. As a result, it is able to ensure that the supplied power of the present invention is stable. At this moment, if the power service is terminated, the power stored in the battery is applied to supply with a DC power. Furthermore, the battery control unit 2 can be adopted as a charge/discharge controller and a remaining power alarm.

The present invention particularly comprises a signal output amount control unit 3, which is a knob. It is apparent that the present invention not only controls a total amount of the signal outputs, but also comprises an independent signal output amount control unit 3, which is a knob, for each one of the signal outputs so as to aim at various therapeutic treatments for deep/shallow positions, physical causes, and physiotherapeutic requirements of various diseases. As a result, it is possible for the present invention to fine-tune these amounts to adjust a bearing degree (amount) for each ill position. Consequently, these signal output amount control units can respectively control the bearing degree (amount) for each ill position of the patient to enable this patient to readily accept these therapeutic procedures. After this fine-tuning adjustment is executed, an overall adjustment is performed by means of controlling the total amount.

Moreover, the connection ports (port 1, port 2 through port N) of the central processing unit 10 of the present invention connect to at least one signal output shift control unit 4, wherein each signal output shift control unit 4 cooperates with a sub-system (A1) that comprises a signal transformation unit 15, a signal output driving unit 16, a signal output display unit 17, a signal output actuation unit 18, and an overvoltage protection unit 19, and a signal output amount control unit 3.

The central processing unit 10 of the present invention is able to connect with a plurality of sub-systems via a plurality of connection ports so as to utilize the time difference for applying the intermittent therapeutic procedure to the treated portions of the patient (this patient can be affected by peaks of waves that occur in different time). Moreover, the therapeutic efficacy can be achieved by use of the central processing unit 10 to perform the controlling and adjusting steps in time domain.

In addition, the present invention is able to comprise a dynamic overvoltage protection unit in response to the degree that this patient can bear with, wherein the dynamic overvoltage protection unit and a static overvoltage protection unit can be switched into one another. As a result, when this patient undergoes the therapeutic procedure, he is able to set an initial total amount by himself according to the degree that he can bear with. Besides, regarding to the aspect of the dynamic overvoltage protection, a fixing step is performed immediately after the signal is outputted. In other words, a fixing step is performed immediately to fix on a specific value of the output amount if this specific value is output. As long as the aforementioned unusual phenomenon occurs or the value of the output amount exceeds this specific value as a result of man-made operation, the signal output actuation unit will be terminated immediately to stop the signal output. Naturally this patient can disable the dynamic overvoltage protection and can merely enable the predetermined static overvoltage protection. Consequently, the dynamic overvoltage protection unit provides with the purposes of fixing and protection when the voltage becomes too large.

The aforementioned forming procedures are performed by use of an editing and display unit of a LCD monitor. Moreover, each formed modulated wave group can be treated as a single formula (for example, the modulated wave groups shown in FIGS. 3, 4, 6, 7, 9, and 10). For this single formula, the editing step and the practical test step can be performed simultaneously, or if any one of the parameter values (as shown in FIGS. 2, 5, and 8, FIGS. 3 and 4, FIGS. 6 and 7, and FIGS. 9 and 10) is changed in the practical test step, its function diagram or frequency or magnitude of the modulated wave groups will be also changed. If any one of the modulated wave groups (formulas) is applied to the human body, a corresponding electrobiological affect is generated. The parameter value is adjusted until it is practically suitable for the pathological treatment for the human body. In this condition, this formula can be stored in the data-memorizing unit for use in the later forming step of a therapeutic procedure. In the forming step of the therapeutic procedure, all of the modulated wave groups (FIGS. 3, 4, 6, 7, 9, and 10) are edited and connected with one another in various sequences to form the therapeutic procedure. After that, the therapeutic procedure are stored in the data-memorizing unit 11 for use in the later treatment. In accordance with the same principle, the therapeutic procedure can be alternatively formed in the same way as the aforementioned single formula until it is practically suitable for the pathological treatment of the human body. This therapeutic procedure is thereafter stored in the data-memorizing unit 11 for use in the later therapeutic treatment. In this manner, a complete and changing therapeutic procedure is formed. The efficacy of the electrotherapy with the modulated medium frequency carrier wave on the physiological treatment is described in the following.

1. The medium frequency wave is a kind of infiltration force. The magnitude of the infiltration force is in direct direction to that of the frequency. On the contrary, the medium frequency wave that does not undergo the modulation process is a pure medium frequency wave and the infiltration force of which is not obvious.

2. The low frequency wave is a kind of applied force. The magnitude of the applied force is in inverse proportion to that of the frequency. On the contrary, the low frequency wave and the extremely low frequency wave that do not undergo the modulation process are a pure low frequency wave and a pure extremely low frequency wave respectively. They easily cause the patient to suffer discomfort since the applied forces of the low frequency wave and the extremely low frequency wave are very strong. Moreover, the electrolysis phenomenon generated by the low frequency wave and the extremely low frequency wave also damages the patient's skin easily.

As described above, if the infiltration force exists in the absence of the applied force, the infiltration force is not sufficient to excite the nervous tissue and the musculature. On the contrary, if the applied force exists in the absence of the infiltration force, the applied force is merely confined to a surface layer of the skin and makes the patient unconformable. Moreover, the electrolysis phenomenon generated by the low frequency wave and the extremely low frequency wave damages the patient's skin easily.

Consequently, after these two kinds of forces are combined, the medium wave is directly applied to the human body, and the modulated low frequency wave and the extremely low frequency wave (modulated waves) permeate into the human body in accordance with magnitude variations of the medium frequency wave. As a result, larger electrotherapeutic efficacy on deeper portions of the human body is obtained during the physiotherapeutic treatment.

While an embodiment of the present invention has been illustrated and described, various modifications and improvements can be made by those skilled in the art. The embodiment of the present invention is therefore described in an illustrative but not restrictive sense. It is intended that the present invention may not be limited to the particular forms as illustrated, and that all modifications which maintain the spirit and scope of the present invention are within the scope as defined in the appended claims.

What the invention claimed is:

1. An electrotherapeutic apparatus for programming and memorizing modulated medium frequency carrier waves, which is applied to memorize modulated wave groups for use in deep/shallow positions, physical causes, and therapeutic procedures of diseases to provide with suitable and accurate therapeutic procedures, the electrotherapeutic apparatus comprises:

a central processing unit, which is adopted as an operation center of the electrotherapeutic apparatus and cooperated with a program-memorizing unit for storing program (software);

a data-memorizing unit, electrically connected with the central processing unit for storing data of modulated wave groups of modulated low frequency waves and extremely low frequency waves (modulated waves) and the therapeutic procedures;

a data input unit, electrically connected with the central processing unit for choosing or editing the data of the modulated wave groups stored in the data-memorizing unit;

an alarm/output unit, electrically connected with the central processing unit for warning and outputting statuses of the electrotherapeutic apparatus;

an editing and display unit, electrically connected with the central processing unit for displaying the data of the modulated wave groups stored in the data-memorizing unit;

a signal transformation unit, electrically connected with the central processing unit for performing a digital/ analog conversion step on the data of the modulated wave groups so as to form the modulated wave groups;

a signal output driving unit, electrically connected with the signal transformation unit for driving the signal transformation unit;

a signal output display unit, electrically connected with the signal transformation unit for displaying signal output statuses of the electrotherapeutic apparatus;

a signal output actuation unit, electrically connected with the central processing unit and the signal output driving unit respectively, wherein the central processing unit drives the signal output actuation unit to utilize two independent signal output ports through the signal output driving unit to output synchronous signals; and an overvoltage protection unit, electrically connected with the central processing unit and the signal output actuation unit respectively, wherein when the supplied power is unstable or an interference source generates a surge, the signal output actuation unit will be terminated to stop outputting signals to avoid the overvoltage phenomenon.

2. The electrotherapeutic apparatus for programming and memorizing modulated medium frequency carrier waves of claim 1 wherein the program-memorizing unit is mounted inside the central processing unit to form an internal program-memorizing unit.

3. The electrotherapeutic apparatus for programming and memorizing modulated medium frequency carrier waves of claim 1 wherein the program-memorizing unit is mounted outside the central processing unit and electrically connected to thereof to form an external program-memorizing unit.

4. The electrotherapeutic apparatus for programming and memorizing modulated medium frequency carrier waves of claim 1 wherein medium square waves ranged from 2 KHz to 10 KHz are adopted as carry waves, which are modulated to form the modulated waves.

5. The electrotherapeutic apparatus for programming and memorizing modulated medium frequency carrier waves of claim 1 wherein the modulated waves are at low frequencies (from 2 Hz to 150 Hz) and/or extremely low frequencies (from 0.2 Hz to 2 Hz) or much lower frequencies.

6. The electrotherapeutic apparatus for programming and memorizing modulated medium frequency carrier waves of claim 1 wherein the data input unit is a push button.

7. The electrotherapeutic apparatus for programming and memorizing modulated medium frequency carrier waves of claim 1 wherein the alarm/output unit is a speaker.

8. The electrotherapeutic apparatus for programming and memorizing modulated medium frequency carrier waves of claim 1 wherein the editing and display unit is a liquid crystal display monitor.

9. The electrotherapeutic apparatus for programming and memorizing modulated medium frequency carrier waves of claim 1 wherein the signal output display unit is a light emitting diode.

10. The electrotherapeutic apparatus for programming and memorizing modulated medium frequency carrier waves of claim 1 wherein the signal output actuation unit comprises two independent non-contact switches to permit or forbid outputting the signals.

11. The electrotherapeutic apparatus for programming and memorizing modulated medium frequency carrier waves of claim 1 wherein the data input unit further comprises a shortcut button for simplifying the input operation.

12. The electrotherapeutic apparatus for programming and memorizing modulated medium frequency carrier waves of claim 1 wherein the central processing unit connects to a battery control unit.

13. The electrotherapeutic apparatus for programming and memorizing modulated medium frequency carrier waves of claim 1 wherein the signal output actuation unit further connects to a signal output amount control unit for every signal output.

14. The electrotherapeutic apparatus for programming and memorizing modulated medium frequency carrier waves of claim 1 wherein connection ports of the central processing unit connect to at least one signal output shift control unit, and each signal output shift control unit cooperates with a sub-system that comprises a signal transformation unit, a signal output driving unit, a signal output display unit, a signal output actuation unit, and an overvoltage protection unit, and a signal output amount control unit.

15. The electrotherapeutic apparatus for programming and memorizing modulated medium frequency carrier waves of claim 1 wherein the signal output display unit is connected to a dynamic overvoltage protection unit to enable a patient to perform a fixing step by himself to avoid an improper operation, and the signal output display unit is connected to a static overvoltage protection unit such that the dynamic overvoltage protection unit and the static overvoltage protection unit can be switched into one another.

* * * * *